US012577220B2

(12) United States Patent
Len et al.

(10) Patent No.: US 12,577,220 B2
(45) Date of Patent: Mar. 17, 2026

(54) METHOD FOR MANUFACTURING (2,2-DIMETHYL-1,3-DIOXOLAN-4-YL) METHANOL

(71) Applicants: DEASYL SA, Plan-les-Ouates (CH); ECOLE NATIONALE SUPERIEURE DE CHIMIE DE PARIS, Paris (FR); CENTRE NATIONAL DE LA RECHERCHE SCIENTIFIQUE, Paris (FR)

(72) Inventors: Christophe Len, Villers sur Coudun (FR); Mohamad Khodadadi, Paris (FR); Julien Thiel, Arbusigny (FR); François Lacoste, Neuilly-sur-Seine (FR)

(73) Assignees: DEASYL SA, Plan-les-Ouates (CH); ECOLE NATIONALE SUPERIEURE DE CHIMIE DE PARIS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 912 days.

(21) Appl. No.: 17/782,075

(22) PCT Filed: Dec. 1, 2020

(86) PCT No.: PCT/EP2020/084143

§ 371 (c)(1),
(2) Date: Oct. 4, 2022

(87) PCT Pub. No.: WO2021/110688

PCT Pub. Date: Jun. 10, 2021

(65) Prior Publication Data

US 2023/0242500 A1 Aug. 3, 2023

(30) Foreign Application Priority Data

Dec. 3, 2019 (FR) ...................................... 1913682

(51) Int. Cl.

| | |
|---|---|
| ***C07D 317/20*** | (2006.01) |
| ***B01J 8/18*** | (2006.01) |
| ***B01J 8/22*** | (2006.01) |

(52) U.S. Cl.

CPC .......... *C07D 317/20* (2013.01); *B01J 8/1836* (2013.01); *B01J 8/1872* (2013.01); *B01J 8/226* (2013.01); *B01J 2208/00061* (2013.01); *B01J 2208/00327* (2013.01); *B01J 2208/00867* (2013.01)

(58) Field of Classification Search

CPC .................................................... C07D 317/20
See application file for complete search history.

(56) References Cited

FOREIGN PATENT DOCUMENTS

WO 2009/141702 11/2009

OTHER PUBLICATIONS

Da Silva et al., "Solvent free heteropolyacid-catalyzed glycerol ketalization at room temperature", RSC Advances, 2015, vol. 5, pp. 44499-44506.
Nanda et al., "Thermodynamic and kinetic studies of a catalytic process to convert glycerol into solketal as an oxygenated fuel additive", Fuel, 2014, vol. 117, pp. 470-477.
De Torres et al., "Glycerol ketals: Synthesis and profits in biodiesel blends", Fuel, 2012, vol. 94, pp. 614-616.
International Search Report for PCT/EP2020/084143, mailed Jan. 26, 2021, 4 pages.
Written Opinion of the ISA for PCT/EP2020/084143, mailed Jan. 26, 2021, 4 pages.
Clarkson et al., "Continuous Reactor Technology for Ketal Formation: An Improved Synthesis of Solketal" Organic Process Research & Development, American Chemical Society and Rhe Royal Society of Chemistry, vol. 5, No. 6, 2001, pp. 630-635.
Reichstein et al., "Überführung de Salze von acetonierten Zuckersauren in ihre Methylester", Helvetica CH/MICA ACTA vol. 18, No. 1, 1925, pp. 598-601.
Guidi et al., "Towards a Rational Design of a Continuous-Flow Method for the Acetalization of Crude Glycerol: Scope and Limitations of Commercial Amberlyst 36 and $AlF_3$ $3H_2O$ as Model Catalysts", Molecules, vol. 21, No. 5, May 18, 2016, pp. 1-19.
Talebian-Kiakalaieh et al., "A Review on the Catalytic Acetalization of Bio-renewable Glycerol to Fuel Additives", Frontiers in Chemistry, vol. 6, Nov. 26, 2018, pp. 1-25.

*Primary Examiner* — Matthew P Coughlin
(74) *Attorney, Agent, or Firm* — NIXON & VANDERHYE

(57) ABSTRACT

A method for manufacturing solketal ((2,2-Dimethyl-1,3-dioxolan-4-yl)methanol) includes: (1) milling starting reagents, including at least: glycerol, a catalyst selected from a hard Lewis acid including at least one transition metal, and acetone, the molar ratio (glycerol):(acetone) being less than or equal to 0.8; preferably less than or equal to 0.7, at an ambient temperature greater than or equal to 50° C., preferably greater than or equal to 56° C., in a three-dimensional microbead mill in a liquid phase for a residence time less than or equal to 15 minutes, preferably less than or equal to 10 minutes, and in particular less than or equal to 5 minutes; (2) recovering, as output from the mill, a final composition including solketal and, where appropriate, one or more sub-products corresponding to the starting reagents that have not reacted and/or to 1,3-O-isopropylidene-glycerol, and (3) optionally, separating the solketal from the one or more sub-products.

21 Claims, 3 Drawing Sheets

Figure 1:
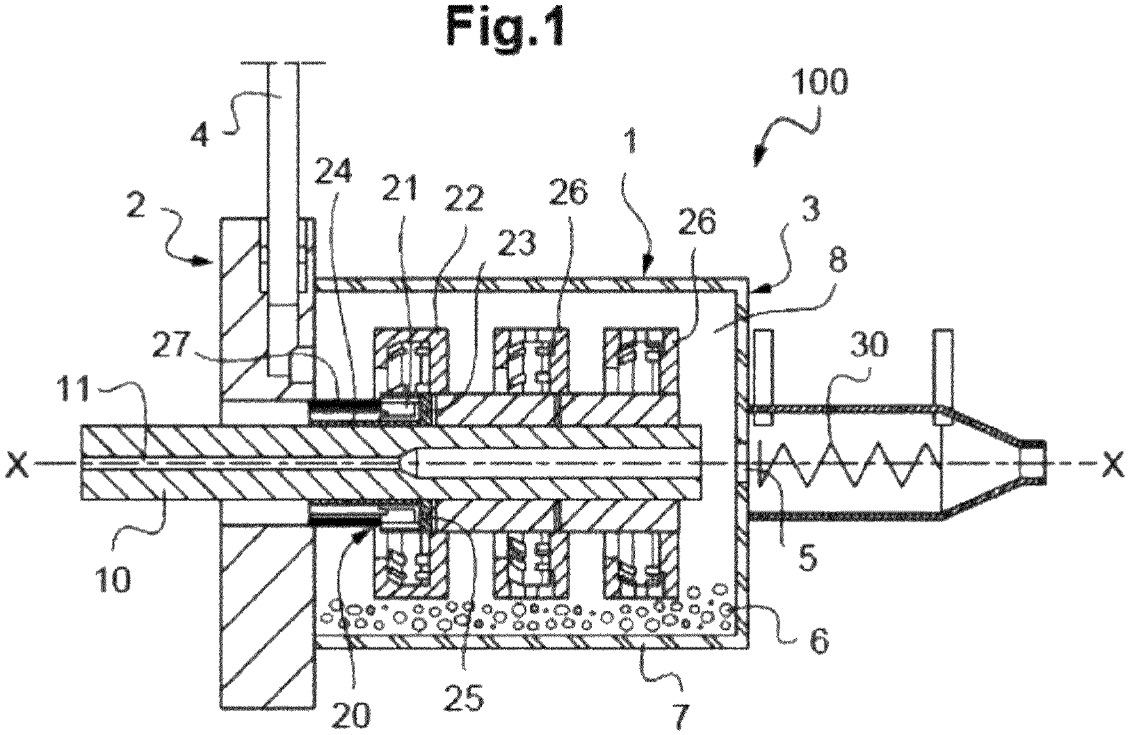

[Fig. 2]
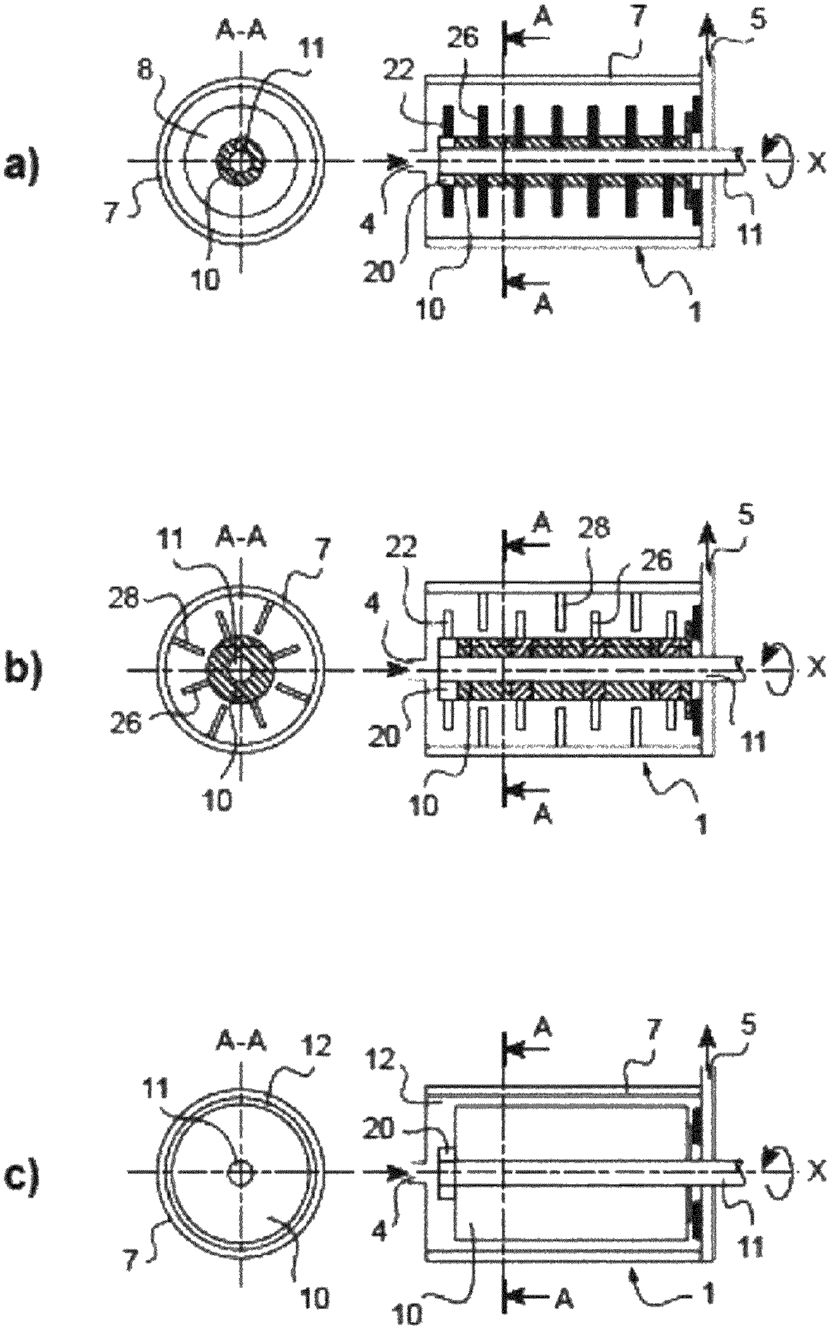

[Fig. 3]
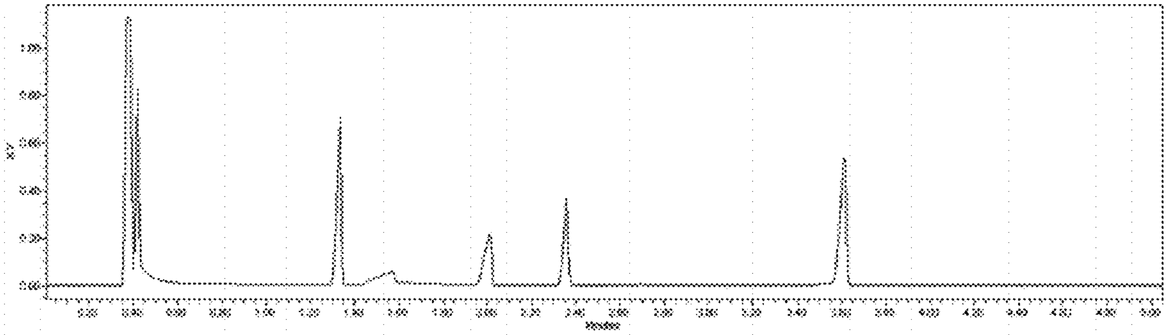
[Fig. 4]
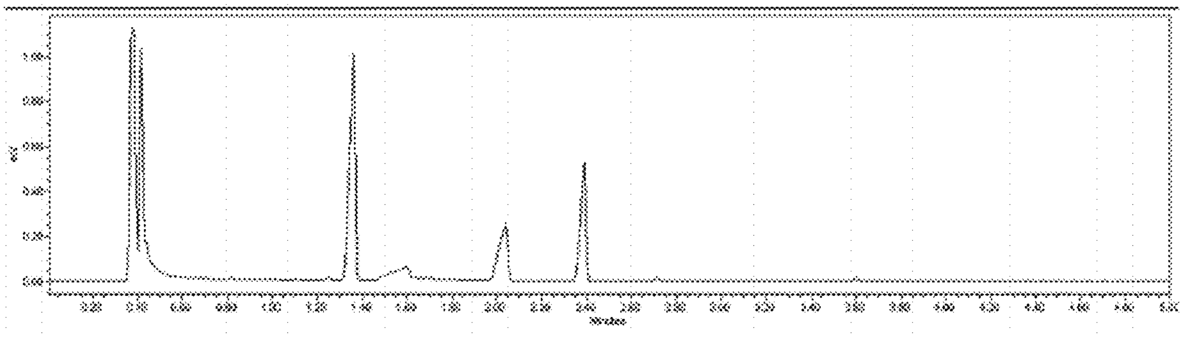

METHOD FOR MANUFACTURING (2,2-DIMETHYL-1,3-DIOXOLAN-4-YL) METHANOL

This application is the U.S. national phase of International Application No. PCT/EP2020/084143 filed Dec. 1, 2020, which designated the U.S. and claims priority to FR 1913682 filed Dec. 3, 2019, the entire contents of each of which are hereby incorporated by reference.

TECHNICAL FIELD OF THE INVENTION

The present invention refers to a method for manufacturing (2,2-Dimethyl-1,3-dioxolan-4-yl)methanol, also known as solketal.

In particular, the present invention relates to a method for manufacturing solketal, conducted by micro-milling at a certain temperature a starting mixture comprising at least glycerol, acetone and a particular catalyst.

STATE OF THE ART

Solketal (2,2-Dimethyl-1,3-dioxolan-4-yl)methanol, also known as 1,2-O-isopropylidene-glycerol, N° CAS 100-79-8) is a molecule comprising an isopropylidene moiety and a hydroxymethyl moiety corresponding to the formula Chem. 1 below.

[Chem. 1]

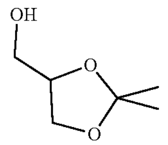

Solketal is a compound useful in many fields, for example in the pharmaceutical field as a synthesis intermediate, in the polymer field as a solvent and plasticizer (Maksimov et al., "Preparation of High Octane Oxygenate Fuel Components from Plant Derived Polyols" *Pet. Chem.* 51, 61-69, (2011)). Solketal also showed interesting properties as a fuel additive by increasing the octane rating and decreasing the gum formation (Mota et al., "Glycerin derivatives as fuel additives: the addition of glycerol/acetoneketal (solketal) in gasolines", *Energy Fuels* 24, 2733-2736 (2010); Silva et al., "Glycerolacetals as anti-freezing additives for biodiesel", *BioresourTechnol.* 101, 6225-6229 (2010) and Garcia et al., New class of acetal derived from glycerin as a biodiesel fuel component", *Energy Fuels* 22, 4274-80 (2008)).

Generally, the solketal is prepared by acetalization from glycerol and

[Chem. 2]

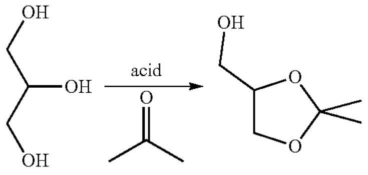

acetone or 2,2-dimethoxypropane in acid medium (Chem. 2 below).

[Chem. 2]

The acid catalyst used to carry out the synthesis reaction is generally a homogeneous catalyst such as $H_2SO_4$, HCl, but other acids can be used, such as Lewis acids or heterogeneous acid catalysts (Talebian-Kiakalaieh et al., "A review on the catalytic acetalization of bio-renewable glycerol to fuel additives", *Front. Chem.* 6, 573, (2018)). In most cases, the reaction is carried out in a batch reactor, although some examples show the possibility of using a continuous reactor.

Different methods for manufacturing solketal have been proposed in the prior art.

The publication of Torres et al., "*Glycerolketals: synthesis and profits in biodiesel blends" Fuel* 94, 614-616, (2012) particularly describes reacting glycerol (10.9 mmol) in acetone in excess (106 mmol) in the presence of sulfuric acid (0.10 mmol) as a homogeneous acid catalyst at 35° C. for 1 hour. After evaporation of the acetone, a saturated solution of $NaHCO_3$ and ethyl acetate are added and the organic phase is evaporated to afford the solketal with a yield of 80%. The use of sulfuric acid as a catalyst however requires a neutralization and extraction step. Yet, the extraction step leads to a significant loss of solketal in the aqueous phase (in the order of 20%).

The publication of Nanda et al., "Thermodynamic and kinetic studies of a catalytic process to convert glycerol into solketal as an oxygenated fuel additive", *Fuel* 117, 470-477, (2014), describes reacting glycerol (197 mmol) and acetone in excess (394 mmol) in the presence of Amberlyst (1 mass %) as an acid heterogeneous catalyst in ethanol (197 mmol) at 25° C. for 3.7 hours. In these conditions, the solketal is obtained with a yield of 74%. The use of ethanol in an equimolar amount allows glycerol and acetone to be solubilized.

The publication of Da Silva et al., "Solvent-free heteropolyacid-catalyzed glycerol ketalization at room temperature", *RSC. Adv.* 5, 44499-44506, (2015), describes reacting glycerol (9.23 mmol) in the presence of heteroacid $H_3PW_{12}O_{40}$ (3 molar % in $H^+$) as an acid homogeneous catalyst in acetone (185 mmol) as a solvent at 25° C. for 2 hours. This leads to the solketal with a yield of 82% (conversion 83%, selectivity 98%).

WO 2009/141702 describes a method for manufacturing solketal which is obtained in continuous flow through reaction between glycerol and acetone at a temperature ranging from 50 to 150° C. The latter is added in small amounts (5 to 20 mol %) to each cycle at 60° C. After several hours of continuous flow (from 2 to 8 hours, generally from 3 to 6 hours), the solketal is obtained.

During this reaction, the acetone is first protonated, which increases its electrophilia. The non-binding pair of the nucleophilic glycerol primary hydroxyl attacks the carbon atom of the activated acetone. After deprotonation of the glycerol primary hydroxyl and protonation of the quaternary hydroxyl, the lone pair of the nucleophilic glycerol secondary hydroxyl attacks the carbon atom releasing a water molecule. The last step is the deprotonation releasing the acid catalyst (cf. Chem. 3 below).

[Chem. 3]

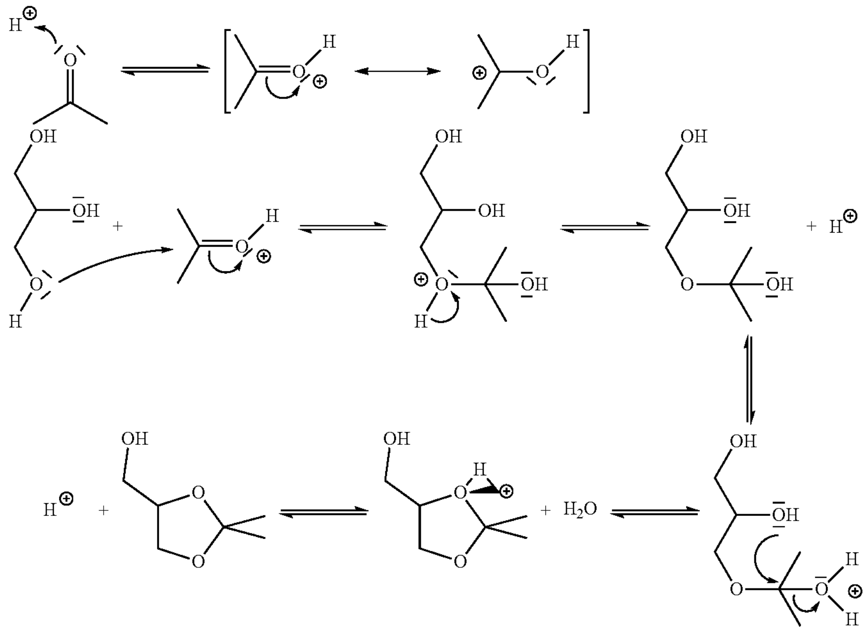

However, the acetalization reaction of the glycerol into solketal has some drawbacks since it generally requires the use of homogeneous or heterogeneous acid in a large catalytic amount (amount by mass greater than 0.004% in relation to the total mass of the starting compounds) in a long reaction time greater than 1 hour. The main obstacle to the solketal production is the low equilibrium constant. To overcome this problem, the use of a high acetone-glycerol ratio or the trapping of the formed water makes it possible to increase solketal productivity by shifting the equilibrium of the reaction.

Thus, these prior art methods suffer from the fact that they either have an unsatisfactory yield or require a high temperature and/or a very long reaction time (which can range for example from 2 to 8 hours).

The publication of Amin Talebian-Kiakalaieh et al., "A review on the catalytic acetalization of bio-renewable glycerol to fuel additives", *Frontiers in Chemistry*, November 2018, lists the numerous methods of glycerol catalytic acetalization, and especially the reaction with acetone in order to prepare solketal.

There is therefore a need in the state of the art for new methods for manufacturing solketal, preferably industrially usable, that are alternatives or improved with respect to known methods.

The object of the present invention is therefore to provide a method for manufacturing solketal, which at least partly avoids the above-mentioned disadvantages. In particular, the present invention is intended to provide a new method for manufacturing solketal which is industrially usable, while not requiring too much heating and/or too long reaction time.

PRESENTATION OF THE INVENTION

To this end, the present invention proposes a method for manufacturing (2,2 dimethyl-1,3-dioxolan-4-yl)methanol (hereafter referred to as solketal) which comprises at least the following steps:

(1) milling the following reagents, called starting reagents, comprising at least: glycerol, a catalyst selected from a hard Lewis acid containing at least one transition metal, and acetone, the molar ratio (glycerol):(acetone) being less than or equal to 0.8, preferably less than or equal to 0.7, at a room temperature greater than or equal to 50° C., preferably greater than or equal to 56° C., in a three-dimensional microbead mill for a residence time less than or equal to 15 minutes, preferably less than or equal to 10 minutes and in particular less than or equal to 5 minutes;

(2) recovering, at the mill outlet, a final composition comprising the solketal and, where applicable, one or more by-products corresponding to the unreacted starting reagent(s) and/or 1,3-O-isopropylidene-glycerol, and (3) optionally, separating the solketal from said by-product(s).

The inventors have developed a method which, surprisingly and unexpectedly, allows the synthesis of solketal at a relatively low temperature (about 50° C.-70° C.), in a single milling step, and in a very short time (the residence time of the reagents in the mill is less than 15 minutes and is generally less than 5 minutes versus 2 to 8 hours for the method according to WO 2009/141702).

As will be demonstrated in the experimental tests below, the method of the invention using a particular mill, namely a microbead three-dimensional mill, combined with particular reaction conditions (selection and molar concentration of the starting reagents, reaction temperature, throughput, etc.) makes it possible to manufacture solketal with a yield generally equal to or greater than 80% and especially equal to or greater than 99%.

The method according to the invention has also the advantage of a very low cost price (indeed, the raw materials used are widely available, non-polluting and inexpensive) and excellent reproducibility, which further sets it apart from the methods described in the prior arts. The method according to the invention has also the advantage that it can be implemented continuously. Yet, these characteristics are important for an industrial scale application.

Moreover, despite the extensive research conducted on the solketal synthesis, none of them suggested the above-mentioned method and in particular a milling step in a microbead three-dimensional mill from the starting reagents.

Other non-limiting and advantageous characteristics of the method for manufacturing solketal according to the invention, taken individually or in all technically possible combinations, are in the following:

- the method comprises a preliminary step (0) wherein the starting reagents including at least glycerol and acetone, or even preferably said catalyst, are pre-mixed to form a starting composition;
- during the preliminary step (0), the starting composition is preheated to a temperature greater than or equal to 50° C., preferably greater than or equal to 56° C., so that the temperature during the milling step (1) is greater than or equal to 50° C., preferably greater than or equal to 52° C. and even more preferably around 56° C.;
- during the milling step (1), the starting reagents are heated within the microbead three-dimensional mill, which includes a heating device, preferably induction heating device;
- the pressure during the milling step (1) is within a range from 0.05 to 20 MPa, preferably from 0.08 to 0.5 MPa, and is typically in the order of 0.1 MPa;
- the hard Lewis acid catalyst comprising at least one transition metal is selected from $FeCl_3$, $AlCl_3$, $CrCl_3$, $MnSO_4$ or a mixture thereof;
- the glycerol is anhydrous or has a water content by mass, relative to the total mass of the glycerol, ranging from 0 to 10%, preferably from 0 to 5%;
- the microbeads are spherical in shape and have an average diameter ranging from 0.05 mm to 4 mm, preferably from 0.2 to 3 mm, in particular from 0.3 to 2 mm and typically in the order of 0.5 to 1 mm;
- the microbeads have a Vickers hardness, measured in accordance with standard EN ISO 6507-1, greater than or equal to 900 HV1, preferably ranging from 900 HV1 to 1600 HV1, typically ranging from 1000 to 1400 HV1;
- the microbeads have an actual density ranging from 2 to 15 g/cm$^3$;
- the milling step (1) is carried out at a room temperature ranging from 50° C. to 70° C., in particular from 55° C. to 60° C. and in general, in the order of 56° C.;
- wherein the microbead three-dimensional mill comprises at least:
- a stationary mill chamber broadly cylindrical in shape, extending along a longitudinal axis XX, said chamber being filled at least in part with said microbeads and comprising: at a first end at least one inlet used to introduce said starting reagents and, at a second end, an outlet comprising a separation means capable of discharging only said final composition;
- an agitator arranged in the stationary mill chamber and taking the form of a rod extending along the longitudinal axis XX, said agitator being capable of setting in motion the microbeads/said starting reagents assembly;
- wherein the microbeads constitute by volume 50% to 85%, preferably 55% to 70%, of the total volume of the stationary chamber;
- wherein the mill operates continuously.

For the rest of the description, unless otherwise specified, the indication of a range of values "from X to Y" or "between X and Y" in the present invention shall be understood as including the values X and Y.

According to the invention, "one or more byproducts" in the final composition correspond to the unreacted starting reagent(s) such as for example catalyst or glycerol (especially if the yield of the reaction is less than or equal to 99%) and where appropriate, a co-product that can be formed during the reaction which is 1,3-O-isopropylidene-glycerol.

Of course, different characteristics, variants and embodiments of the invention can be associated in various combinations with each other as long as they are not mutually exclusive or incompatible.

DETAILED DESCRIPTION OF THE INVENTION

The invention will be better understood and other purposes, details, characteristics and advantages thereof will become clearer when reading the following description of examples of embodiment, with reference to the accompanying figures wherein:

FIG. 1 shows a sectional view, along a cutting plane passing through the longitudinal axis XX, of a three-dimensional mill according to a first embodiment of the invention comprising in particular an induction heating device;

FIG. 2 shows, along cutting planes passing through the longitudinal axis XX and through axis AA, different variants of embodiment of three-dimensional mills according to the invention each comprising a heating device and at least a stirrer which optionally supports another mixing element: (a) the stirrer comprises several other mixing elements in accordance with the mill of FIG. 1, (b) the stirrer further comprises fingers that can cooperate with the other mixing elements and (c) the stirrer does not include mixing elements and fingers;

FIG. 3 shows a chromatogram corresponding to the synthesis of solketal from glycerol after a residence time of 1 minute (reaction time within the three-dimensional mill); and FIG. 4 shows a chromatogram corresponding to the synthesis of solketal from glycerol after a residence time of 2.37 minutes (reaction time within the three-dimensional mill).

It should be noted that in these figures, the structural/functional elements common to the different variants may have the same references.

The inventors focused on the development of a new method for manufacturing solketal adapted to be implemented on an industrial scale and this in a very short time.

Thus, the present invention relates to a method for manufacturing (2,2-Dimethyl-1,3-dioxolan-4-yl)methanol (hereafter referred to as the solketal) which comprises at least the following steps:

(1) milling the following reagents, called the starting reagents, comprising at least: glycerol and a catalyst selected from a hard Lewis acid containing at least one transition metal (hereafter referred to as "the catalyst", with acetone, the (glycerol):(acetone) molar ratio being less than or equal to 0.8, preferably less than or equal to 0.7, at a room temperature greater than or equal to 50° C., preferably greater than or equal to 56° C., in a three-dimensional microbead mill for a residence time less than or equal to 15 minutes, preferably less than or equal to 10 minutes and particularly less than or equal to 5 minutes;

(2) recovering, at the mill outlet, a final composition comprising the solketal and, where applicable, one or more by-products corresponding to unreacted starting reagent(s) and/or 1,3-O-isopropylidene-glycerol, and (3) optionally, separating solketal from said by-product (s).

Generally, the method comprises a preliminary step (0) wherein the starting reagents, including at least glycerol and acetone, and preferably the catalyst, are pre-mixed to form a starting composition.

In particular, the method according to the invention makes it possible to carry out the following synthesis (Chem 4):

[Chem. 4]

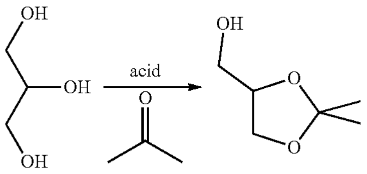

The compound "acid" representing herein the catalyst according to the invention, i.e. the hard Lewis acid catalyst comprising at least one transition metal.

By "hard Lewis acid" according to the invention, it is meant a Lewis acid whose electron-accepting center is weakly polarizable. The hardness criterion of an acid is in particular as defined in the principle Hard and Soft Acid and Base (hereafter HSAB) known to those skilled in the art. Hard acids are for example iron (III), Chromium (IV), aluminum (III), manganese (II), etc. Iron (II) and copper (II) are in a known manner intermediate metal acids and the copper (I) is a soft acid.

Therefore, according to the method of the invention and unlike the methods of the prior art such as the method of WO 2009/141702, the reaction equilibrium is shifted to the formation of solketal; there is no need to trap water or to use a large acetone-glycerol ratio allowing the reaction equilibrium constant to be shifted and thus increasing the solketal productivity.

Optionally, if the reaction is not complete and the solketal yield is greater than or equal to 80% (it depends in particular on the reaction parameters, such as molar proportions of the starting reagents, for example of acetone and/or on the temperature during the milling step), 1,3-O-isopropylidene-glycerol can also be formed as a by-product (Chem 5):

[Chem. 5]

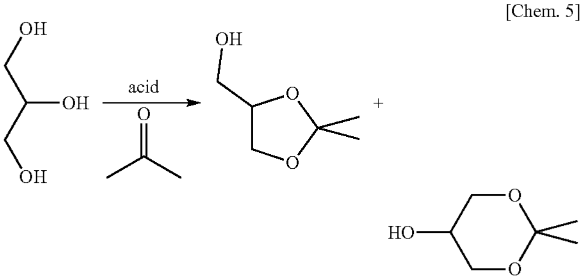

For a better understanding of the method of the invention, a microbead three-dimensional mill capable of synthesizing solketal, and thus being part of the invention, will first be described below with reference to the FIGS. 1 and 2.

As shown in FIGS. 1 and 2, the three-dimensional mill 100 comprises at least one stationary milling chamber 1 having a wall 7 generally cylindrical in shape which envelops an interior 8.

The wall 7 extends along a longitudinal axis XX, advantageously horizontal.

This stationary milling chamber 1 is configured to receive and mix at least the starting reagents, namely glycerol, acetone and catalyst or where appropriate, the starting composition (particular embodiment where the starting reagents are pre-mixed).

This stationary milling chamber 1 is partially filled with at least milling bodies 6 such as microbeads 6 which will allow the reagents to be intensively and efficiently milled and mixed.

The stationary chamber 1 comprises, at a first end 2 (upstream), an inlet 4 which opens into the stationary milling chamber 1 and which serves to introduce the starting reagent (s) or starting composition.

This inlet 4 can also be used to introduce microbeads 6 before implementing the mill 100. As will be seen hereafter, the size and nature of the microbeads 6 may vary slightly.

The milling chamber 100 comprises, at a second end 3 (downstream), an outlet 5 that leads to outside and is configured to discharge the final composition in the stationary milling chamber 1.

The outlet 5 comprises generally a separation means (not shown), such as a sieve or grid, suitable for discharging only the final composition and therefore retaining the microbeads 6 when the mill 100 is in operation.

In particular, the inlet 4 is generally connected to at least one pump, for example peristaltic (not shown). This or these pump(s) allow the starting reagent(s) or the pre-prepared starting composition to be brought inside the stationary milling chamber 1.

The starting reagents or starting composition may be, for example, contained in a container, such as a tank. The pump also allows, during the operation of the three-dimensional mill 100, the starting reagents or starting composition to be fed with a certain flow rate which is adjustable, subsequently referred to as "throughput". This throughput further forms a current in the stationary chamber 1 allowing these starting reagents and/or this starting composition to be driven from the inlet 4 to the outlet 5.

The three-dimensional mill 100 also comprises an agitator 10 which includes an elongated rod 11 along the longitudinal axis XX and which mainly extends around the first end 2 and beyond the second end 3 of the stationary chamber 1.

This elongated rod 11 advantageously extends coaxially to the aforementioned longitudinal axis XX.

This agitator 10 is in particular capable of pivoting so as to set in motion, in addition to the above-mentioned throughput, the milling body 6 and starting reagents/starting composition assembly.

In particular, the agitator 10 is configured to rotate on itself, along the longitudinal axis XX, via an elongated rod 11 (or rotating shaft), to impart within the stationary chamber 1 a swirling motion to the initial mixture and thus effect an intense mixing between this initial mixture and the microbeads 6 in the chamber 1 along the internal surface of the wall 7 of this chamber 1.

In particular, the agitator 10 via its elongated rod 11 can have a rotational speed greater than or equal to 100 revolutions per minute, advantageously greater than or equal to 1000 revolutions per minute (rpm), preferably greater than or equal to 2000 revolutions per minute and typically greater than or equal to 2500 revolutions per minute.

Within the meaning of the invention, "a rotational speed greater than or equal to 100" includes the following values: 100; 150; 200; 250; 300; 350; 400; 450; 500; 550; 600; 650; 700; 750; 800; 850; 900; 950; 1000; 1100; 1200; 1300;

1400; 1500; 1600; 1700; 1800; 1900; 2000; 2100; 2200; 2300; 2400; 2500; 2600; 2700; 2800; 2900; 3000; 3100; 3200; 3300; 3400; 3500; 3600; 3700; 3800; 3900; 4000; 4500; 5000; 5500; 6000; etc., or all intervals between them.

In particular, the rotational speed of the agitator 10 is greater than or equal to 1500 rpm, advantageously greater than or equal to 1600 rpm, in particular greater than or equal to 1800 rpm and typically greater than or equal to 2400 rpm.

In general, the agitator 10 has a rotational speed ranging for example from 1500 rpm to 5000 rpm, in particular from 1550 rpm to 4500 rpm, preferably from 1600 rpm to 4000 rpm and typically from 2400 rpm to 3200 rpm.

Preferably, the peripheral speed of the agitator is greater than or equal to 6 m/s, in particular greater than or equal to 8 m/s.

According to the invention, a peripheral speed of the agitator greater than or equal to 6 m/s includes the following values or any interval between them: 6; 7; 8; 9; 10; 11; 12; 13; 14; 15; 16; 17; 18; 19; 20, etc.

In general, the peripheral speed of the agitator ranges from 7 m/s to 20 m/s, preferably from 8 m/s to 16 m/s.

By "peripheral speed of the agitator", it is meant the rotational speed multiplied by the circumference of the agitator disc.

The rotational speed will be adapted by the one skilled in the art according to the three-dimensional mill used (laboratory mill or industrial mill).

For example, a three-dimensional mill marketed by WAB (Willy A. Bachofen SARL) of the AP05 type has an agitator with the following characteristics: for a frequency of 80 Hz, a speed in revolutions per minute of 4800 and a peripheral speed in m/s of 16.0, while a mill of the AP2 type, for a frequency of 70.8 Hz, has a speed in revolutions per minute of 2730 and a peripheral speed in m/s of 16.0. In order to improve this mixing, the agitator 10, as well as the inner surface of the inner wall 7 of the chamber 1, can have various possible configurations shown for example in FIG. 2.

In a first configuration shown in FIG. 2*a*, the agitator 10 comprises, along his elongated rod 11, "rotary" mixing elements 22, 26 arranged perpendicularly to it.

As will be subsequently described, a mixing element 22 (called "first mixing element") may also correspond to a susceptor of the heating means 20 according to the invention and is thus different from the other mixing elements 26 (called "other mixing elements").

This first mixing element 22, as well as the other mixing elements 26, may correspond to the mixing elements described in U.S. Pat. No. 5,597,126.

In particular, they may include at least two circular discs parallel to each other, configured to set the milling bodies 6 in motion (microbeads).

The number of these mixing elements 22, 26 within the milling chamber 1 can range from 2 to 8, preferably from 2 to 5.

These mixing elements 22, 26 allow, on one hand, for improved milling of the starting reagents and/or starting composition by further stirring the microbeads 6, and on the other hand, accelerate the time of reaction.

In a second configuration shown in FIG. 2*b*, the agitator 10 may also comprise, along its rod 11, one or more "rotary" mixing elements 22, 26 and which are furthermore able to cooperate with the "fixed" fingers 28, arranged perpendicularly to the inner wall 7 of the chamber 1.

A finger 28 is in particular in the form of a ring extending perpendicularly from the wall 7.

For this configuration, the mixing elements 22, 26 and the fingers 28 are arranged in a staggered pattern, namely the mixing elements 22, 26 and the fingers 28 are arranged alternately in the chamber 1.

The fingers 28 thus form counter-fingers, each of which being arranged between two mixing elements 22, 26.

Furthermore, the thickness of the rod 11 is increased in relation to the preceding configuration (FIG. 2*a*) so that the periphery of the mixing elements 22, 26 is close to the inner wall 7 and that of the fingers 28 is close to the periphery of the rod of the agitator 10.

Thus, in this configuration, the chamber volume is decreased in relation to the preceding configuration, thus allowing better mixing between the starting reagents and/or starting composition, microbeads 6 and inner wall 7 of the chamber 1.

In a third configuration, the chamber 1 volume can be further decreased as shown in FIG. 2*c*.

According to this embodiment, the agitator 10 has an inner diameter slightly smaller than the inner diameter of the chamber 1, thus forming an annular chamber 12 of small volume arranged between the outer wall of the agitator 10 and the inner wall 7 of the chamber 1. The microbeads (not shown) are arranged in this annular chamber 12. When operating this third configuration, the starting reagents and/or starting composition are/is introduced through the inlet 4 with a certain flow rate, which will then travel through the annular chamber 12 to the outlet 5, while being stirred by the microbeads 6.

The geometry of the milling chamber 1 and the agitator 10 can be adjusted by the one skilled in the art according to the desired yield, as well as the desired time of reaction. For example, it is also possible that the milling chamber 1 includes an accelerator in order to improve the milling of the initial mixture. This accelerator being known by the one skilled in the art, it will not be detailed hereafter.

In general, the stationary chamber has a diameter of 75 mm to 300 mm for a length of 80 mm to 900 mm and an agitator 10 with a size ranging from 65 mm to 260 mm. Thus, the milling chamber volume can range from 0.35 L to 600 L, preferably, from 0.35 L to 400 L, and typically from 0.35 L to 62 L.

Within the meaning of the invention, "a stationary chamber volume 1 ranging from 0.35 L to 600 L" includes the following values: 0.35; 0.5; 0.8; 1; 2; 3; 4; 5; 6; 7; 8; 9; 10; 15; 20; 25; 30; 35; 40; 45; 50; 55; 60; 65; 70; 80; 85; 90; 100; 110; 120; 130; 140; 150; 160; 170; 180; 190; 200; 210; 220; 230; 240; 250; 260; 270; 280; 290; 300; 350; 400; 450; 500; 550; 600, or all intervals between them.

Preferably, the microbeads 6 accommodated in the milling chamber 3 of the mill 1 during its operation are substantially spherical in shape and have an average diameter less than or equal to 5 mm, generally ranging from 0.05 mm to 4 mm, preferably from 0.2 to 3 mm, in particular from 0.3 to 2 mm, and typically in the order of 0.5 to 1 mm. Preferably, the diameter of the microbeads is less than or equal to 1 mm and is typically in the order of 0.05 mm to 1 mm.

They are preferentially selected from microbeads with high hardness and relatively good abrasion resistance.

In particular, the microbeads 6 have a Vickers hardness, measured in accordance with standard EN ISO 6507-1 (2005) greater than or equal to 900 HV1, preferably ranging from 900 HV1 to 1600 HV1, typically ranging from 1000 to 1400 HV1 and in particular ranging from 110 to 1300 HV1.

Within the meaning of the invention, "a Vickers hardness greater than or equal to 900 HV1" includes the following values: 900; 910; 920; 930; 940; 950; 960; 970; 980; 990; 1000; 1010; 1020; 1030; 1040; 1050; 1060; 1070; 1080; 1090; 1100; 1110, 1120; 1130; 1140; 1150; 1160; 1170; 1180; 1190; 1200; 1300, 1400; 1500; 1600; 1700; etc., or all intervals between them.

Advantageously, they have a high actual density. In general, the microbeads according to the invention have an actual density greater than or equal to 2 g/cm$^3$, in particular ranging from 2 to 15 g/cm$^3$, preferably from 3 to 12 g/cm$^3$, and typically from 4 to 10 g/cm$^3$.

Thus, the microbeads according to the invention can be ceramic microbeads (zirconium oxide $ZrO_2$, in zirconium silicate $ZrSiO_4$); steel microbeads, tungsten carbide microbeads, glass microbeads or a combination thereof.

Preferably, the microbeads are in ceramic because they do not generate pollution through wear.

In particular, the microbeads are in zirconium oxide.

Optionally, the zirconium oxide microbeads can be stabilized by another oxide, such as cerium oxide, yttrium oxide and/or silicon.

By way of examples, the following compositions, summarized in Table 1 below, are suitable for forming the microbeads according to the invention:

TABLE 1

| Microbead composition | Hardness HV1 | Actual density (g/cm$^3$) | Manufacturer |
|---|---|---|---|
| Zirconium oxide microbeads stabilized with cerium oxide 80% $ZrO_2$ 20% CeO | 1180 | ≥6.10 | Saint-Gobain (Zirmil ®YCeramicBeads) or EIP (Procerox ® ZO Cer) |
| Zirconium oxide microbeads stabilized with yttrium 95% $ZrO_2$ <5% $Al_2O_3$ Remainder: $Y_2O_3$ | 1250 | ≥5.95 | EIP (Procerox ® ZO (Y)) |
| Zirconium oxide microbeads stabilized with yttrium and silicon: 78% $ZrO_2$, 12% $SiO_2$, 5% $Al_2O_3$ and 4% $Y_2O_3$ | >700 | >4.80 | Saint-Gobain (ER120 CeramicBeads) |
| Zirconium silicate microbeads $ZrSiO_4$ | ≥800 | >6.5 | Saint-Gobain (RimaxCeramicBeads) |
| Glass microbeads | 500 | >3.76 | — |
| Steel microbeads | 700 | >7.7 | — |

Generally, the microbeads 6 suitable for the invention are not made of glass or exclusively of glass.

In particular, the microbeads 6 represent by volume, in relation to the total volume of the stationary chamber 2, from 50% to 85%, preferably from 55% to 70%.

Within the meaning of the invention, "a volume from 50 to 85%" includes the following values: 50; 55; 60; 65; 70; 75; 80; 85; etc., or all intervals between them.

The solketal synthesis reaction is carried out under heat, i.e. at a temperature greater than or equal to 50° C., preferably greater than or equal to 52° C. and ideally greater than or equal to 56° C. in order to obtain a better yield.

Indeed, the boiling temperature of acetone is 56.05° C. at atmospheric pressure. That is why, advantageously, the reaction temperature within the mill is around 56° C.

According to a first embodiment, in order to obtain this temperature of at least 50° C. and preferably 56° C., the starting reagents and/or starting composition are pre-heated. Thus, there is no need to heat or have a heating device within or around the microbead three-dimensional mill.

For example, according this embodiment, in the preliminary step (0), the starting composition is heated at a temperature greater than or equal to 50° C., preferably greater than or equal to 56° C., so that the temperature in the milling step (1) is greater than or equal to 50° C., preferably greater than or equal to 56° C.

Indeed, as the residence time of the starting reagents or starting composition within the mill is very short (in general, lower than or equal to 5 minutes, preferably lower than or equal to 2 minutes), the heating of the starting reagents and/or starting composition is sufficient.

However, this embodiment requires special attention, especially at the start of the reaction when the mill is cold or when changing the flow rate.

According to a second embodiment, which can be combined with the first one, the temperature of at least 50° C. and ideally 56° C. can be reached in the three-dimensional mill.

For this purpose, in the milling step (1), the starting reagents and/or starting composition are heated in the microbead three-dimensional mill which comprises at least one heating device, preferably at least one induction heating device 20. This embodiment has the advantage of a more accurate reaction temperature regardless of the flow rate or the temperature of the starting reagents/starting composition at the mill inlet (better heating of the flow forming the starting mixture). This embodiment is also particularly suited for an embodiment wherein several successive grindings are carried out on the same mixture.

For example and as shown in FIG. 1, the induction heating device(s) 20 are integrated inside the stationary milling chamber 1 and allow the heating of at least one area of said stationary milling chamber 1.

According to a characteristic of the invention, the induction heating device(s) 20 are located at the entrance of the chamber 1, i.e. around the first end 2 so that the initial mixture flow can be heated (starting reagents/starting composition) upon introduction and thus enable and/or activate the chemical synthesis of solketal.

According to a preferred embodiment of the invention, the induction heating device 20 is carried by at least part of said agitator 10, allowing the rotary movement of the induction heating device 20 around the longitudinal axis XX.

Generally, the induction heating device 20 comprises:

- at least one inductor 21, capable of generating magnetic field, and
- at least one electrically conductive susceptor 22, which is coupled to said inductor 21 and capable of being heated thereby 21.

In particular, the inductor 21 is a coil or a solenoid with turns that surround part of said rod 11 of the agitator 10, advantageously an upstream section on side of the first end 2 as shown in FIG. 1.

The inductor 21 is particularly suitable for generating a magnetic field which will allow the heating of the conductive materials in its environment, and in particular the susceptor 22 to which it is coupled. Indeed, the susceptor 22, which is electrically conductive, is able to capture the magnetic field emitted by the inductor.

The coil and susceptor assembly can be rotated by the rod 11.

The other mixing elements 26, which are different from the first mixing element 22, namely they are not necessarily electrically conductive, may in particular be made of chromium casting or zirconium oxide-type ceramic.

Referring to FIG. 1, this first mixing element 22 usually has a base that is integral with the rod 11 of the agitator 10. Preferably, the inductor 21 is located at this base.

Usually, the induction heating device 20 is connected to an alternating electric current generator disposed outside said milling chamber 1 through at least one current supply means 27 which is coaxial with the rod 11 of the agitator 10.

In particular, the generator can have an output ranging from 5 to 15 kW and preferably 10 kW with a frequency ranging for example from 17 to 200 kHz. It has a capacity box which can be parallel or in series. As an example, a generator in series ID Partner, reference IX3600 model PO8010 is suitable to achieve the mill of the invention.

In general, the stationary milling chamber 1 incorporates a magnetic shield 23 arranged between said inductor 21 and said rod 11 of the agitator 10 so as to direct the heating towards the initial mixture.

Indeed, it might be that the agitator 10 or its rod 11 is made of electrically conductive material and thus, in order to avoid overheating of the agitator 10, it is preferred to protect the agitator 10 or at least the rod 11 part which is surrounded by the inductor 21.

This magnetic shield 23 has also the advantage of directing the magnetic field emitted by the coil 21 to the first mixing element 22 so that all power is concentrated outside the inductor and in particular is not directed towards the rod 11. Thus, the heating zone is restricted to the outer periphery of the rod 11 and particularly concentrated on the first mixing element 22.

Such a mill incorporating a heating device is described in particular in the application FR 18 54592.

As mentioned above, it is possible to combine the first and second embodiment. Thus, according to a third embodiment, the temperature of at least 50° C. and ideally 56° C., is reached by combining a prior preheating according to the first embodiment and an internal heating to the mill according to the second embodiment.

By way of example, the microbead three-dimensional mill in liquid phase suitable for carrying out the method according to the invention may correspond to mills sold by the companies WAB, Dyno-Mill range: Multi Lab, ECM and KD, NETZCH or Alpine Hosokawa, for example, Agitated Media Mill AHM or to those types of mills wherein a heating device as described above has been incorporated.

The manufacturing method according to the invention will now be described more explicitly below.

In particular, we will describe in more details below the embodiment comprising the preliminary step (0) for preparing the starting composition, although this is not a limitation of the invention. Indeed, as already mentioned before, the starting reagents can be directly introduced in the mill 100.

Thus, advantageously, the solketal manufacturing according to the invention may comprise a preliminary step (0) for preparing the starting composition. Indeed, it is generally easier from a practical point of view to prepare starting composition comprising the different starting reagents in the desired proportions. Optionally, the catalyst according to the invention can be added subsequently in the three-dimensional mill 100.

Thus, glycerol is mixed with acetone in a molar ratio (glycerol:acetone) lower than or equal to 0.8, preferably lower than or equal to 0.7.

According to the invention, a molar ratio (glycerol:acetone) lower than or equal to 0.8 includes the following ratios and all intervals between them: 0.8; 0.7; 0.6; 0.5; 0.4; 0.3; 0.2; 0.1, etc.

In particular, the molar ratio is also greater than or equal to 0.1, preferably greater than or equal to 0.2 and typically greater than or equal to 0.3, as for example in the order of 0.5.

Typically, the molar ratio (glycerol:acetone) is in the order of 0.5. In contrast to the methods of the prior art, it is not necessary to have a large excess of acetone to carry out the solketal synthesis according to the invention.

The starting composition is conventionally prepared by mixing the starting reagents, namely at least acetone and glycerol and preferably catalyst, in a suitable device, such as a container or a tank, with a stirring system (such as magnetic stirrer, stirring blades, etc.). The device as well as the stirring system can be adapted by the one skilled in the art according to the amount of solketal to be manufactured.

As noted above, the glycerol and acetone are mixed in order to perform the following reaction:

[Chem. 4]

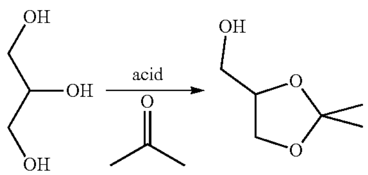

In a known manner, the viscosity of the glycerol decreases very quickly with the temperature, but also with the water content. That is why, preferably, the glycerol used in the method of the invention is anhydrous or has a water content, by mass, in relation to the total mass of the glycerol, ranging from 0 to 10%, preferably, from 0 to 5%.

According to the invention, glycerol comprising a water content ranging from 0 to 10% includes the following values or all intervals between them: 0; 1; 2; 3; 4; 5; 6; 7; 8; 9 or 10%.

The viscosity of the glycerol can be, according to techniques known to those skilled in the art, such as using a vibrating blade viscometer, measured before carrying out the method of the invention and in particular the milling step (1).

The glycerol suitable for the present invention is in liquid form. Glycerol with CAS number: 56-81-5 and sold for example by Mon-droguiste.com, of purity greater than or equal to 99.5%, is suitable for carrying out the method of the invention.

The acetone suitable for the present invention is in liquid form. Acetone with CAS number: 67-64-1 and sold for example by Mon-droguiste.com, of purity greater than or equal to 99.5%, is suitable for carrying out the method of the invention.

Preferably, acetone and glycerol have a high purity, in general greater than or equal to 90%, especially greater than or equal to 95% and typically greater than or equal to 99%, or even greater than or equal to 99.9%.

The catalyst suitable for the method according to the invention is selected from a hard Lewis acid (doublet acceptor) comprising at least one transition metal. In particular, the transition metal is selected from iron, aluminum, manganese or chromium. By way of example, the catalyst according to the invention can be selected from: $FeCl_3$ such as $FeCl_3 \cdot 6H_2O$, $AlCl_3$, $CrCl_3$, $MnSO_4$ or a mixture thereof.

The catalyst represents, by mass, in relation to the total mass of the starting composition comprised of acetone, glycerol and the catalyst, from 0.02% to 1%, preferably from 0.03% to 0.08% and typically from 0.03% to 0.05%, such as 0.044%.

Once the starting composition is prepared, this is fed to the microbead three-dimensional mill 100 generally through the peristaltic pump with adjustable flow rate via inlet 4. The peristaltic pump allows the mixing of the starting composition to continue before entering the stationary chamber 1. Moreover, as previously noted, this pump allows the starting composition to be introduced into the chamber 1 with a controlled throughput.

Generally, the starting composition is introduced at a throughput of 5 to 130 L/h, preferably 10 to 100 L/h and typically 10 to 90 L/h.

According to the invention, "a throughput ranging from 5 to 130 L/h" includes the following values and all intervals between them: 5; 6; 7; 8; 9; 10; 11; 12; 13; 14; 15; 16; 17; 18; 19; 20; 21; 22; 23; 24; 25; 26; 27; 28; 29; 30; 35; 40; 45; 50; 55; 60; 65; 70; 75; 80; 85; 90; 95; 100; 105; 110; 115; 120; 125; 130.

Once the starting composition is introduced in the chamber 1, the milling step (1) starts.

Under the effect of the current created by the throughput, the starting composition passes through the stationary chamber 1 from the inlet 4 to the outlet 5, while being set in motion by the agitator 10 which allows an intense mixing of this composition with the microbeads and, where appropriate, with discs 22; 26, fingers 28, etc., along the inner wall of the chamber 1.

The rotational speed of the agitator may for example vary from 10 to 150 Pi rad/s, preferably from 40 to 100 and in particular from 60 to 70 Pi rad/s and is in particular at least 60 Pi rad/s, such as 63 Pi rad/s.

According to the invention, a rotational speed ranging from 10 to 150 Pi rad/s includes the following values and all intervals between them: 10; 20; 30; 40; 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100; 110; 120; 130; 140; 150. The residence time of the starting suspension is lower than or equal to 15 min.

According to the invention, a residence time lower than or equal to 15 minutes includes the following values and all intervals between them: 15 min; 10 min; 11 min; 10 min; 9 min; 8 min; 7 min; 6 min; 5 min; 4 min; 3 min; 2 min; 1 min; 55 sec: 50 sec; 45 sec; 40 sec; 35 sec; 30 sec; 25 sec; 20 sec; 15 sec; 10 sec, 5 sec, etc.

Preferably, the residence time in the mill is lower than or equal to 10 minutes, and especially ranges from 30 seconds to 8 minutes and in particular from 50 seconds to 5 minutes.

It is indeed inherent in the bulk volume of the beads and the throughput. For example, if the total bulk volume of the beads is 270 $cm^3$ (beads having a bulk density of 3.7 $g/cm^3$) and if the feed rate of the suspension is 45 L/h, that is 12.45 $cm^3/s$, then the residence time of the suspension in the chamber 1 is estimated at approximately 22 seconds. Therefore, the residence time can be advantageously regulated, for example by controlling the bulk density of microbeads as well as the throughput.

By "bulk volume" it is meant the volume of the microbeads including the interstitial air between the beads. The bulk density is the ratio of the mass of the microbeads to the bulk volume.

Preferably, the bulk volume of the microbeads ranges from 250 mL to 450 mL, preferably from 300 mL to 400 mL and typically from 330 mL to 360 mL. This bulk volume of the microbeads is suitable for example for a three-dimensional mill comprising a 500 mL stationary chamber 1.

In addition, by adjusting the size of the microbeads and the throughput, the solketal synthesis may be improved.

Preferably, the pressure during the milling step (1) ranges from 0.05 to 20 MPa, preferably from 0.08 to 0.5 MPa and is typically in the order of 0.1 MPa.

The milling step can be carried out in continuous or batch mode in one or more passes (pendulum or recirculation mode). When it is carried out in batch mode, the number of passes of the starting composition can be from 1 to 10, preferentially from 1 to 5 (namely, after a first pass, the final composition is recovered at outlet 6 and reintroduced by the pump into the chamber 1 via the inlet 4 to allow a second pass). In particular, the number of passes of the starting suspension is 1.

Indeed, the inventors noticed that a single pass through the microbead mill, despite a very short residence time, made it possible to obtain at outlet 5 a final composition comprising mainly solketal.

Thus, this milling step is preferably carried out in continuous mode.

Advantageously, this milling step takes place at a temperature greater than or equal to 50° C., namely, most often at a temperature greater than or equal to 56° C. which is the solketal synthesis temperature in order to obtain a better yield.

Once the milling step is completed, (1) the final composition is recovered from the outlet 5 of the mill 100. This final composition may include traces of unreacted starting reagents, such as for example catalyst or even a byproduct, 1,3-O-isopropylidene-glycerol, if the reaction temperature or the concentrations of the starting reagents were not in the ideal ranges of reaction.

The method according to the invention provides a solketal yield greater than or equal to 80%, preferably greater than or equal to 85% and in particular greater than or equal to 90%.

In general, the method according to the invention provides a solketal yield greater than or equal to 99% (optimized experimental conditions).

The solketal may be separated from the reaction medium (from the starting reactions and/or starting composition, or even the other formed byproduct(s)) in a known manner by methods well known to the one skilled in the art. These methods can be for example by extraction, solvent evaporation (acetone) or distillation.

The solketal can be furthermore purified if necessary by techniques also well known to the one skilled in the art, such as by distillation or silica gel column chromatography or high performance liquid chromatography (HPLC).

EXAMPLES

The description of the following tests is given as a purely illustrative and non-limiting example.

Raw Materials

For the tests, the starting raw materials are:

Glycerol (Fluorochem, Hadfield, UK) Lot FCB019493

$FeCl_3 \cdot 6H_2O$ (Fluorochem, Hadfield, UK) Lot FCB048596

Acetone>99% (Sigma-Aldrich, Steinheim, Germany), Lot #STBJ2303

Mill According to the Invention

The tests were implemented in a microbead three-dimensional mill Dynomill ECM AP-05 of Willly A. Bachofen AG (WAB), which contains 1.235 kg of microbeads, and was adapted to include a heating device 20 according to the invention as shown in FIG. 1. Namely, the mill comprises a heating device positioned at the entrance to the stationary chamber, and the first mixing element acts as a susceptor (patent FR18 54592).

In particular, the heating device has the following characteristics:

TABLE 2

| Elements | Characteristics |
|---|---|
| Generator | 10 kW generator with a frequency ranging from 17 to 200 kHz/generator in series IDPartner reference IX3600 model PO8010. |
| Inductor | Multi-strand Litz wires, resinated to be removable. Cable from IDPartner 300 strands Litz Cu 9.425 $mm^2$ 6 × 50 × 0.2 mm. |
| Susceptor | Mixing element as described in U.S. Pat. No. 5,597,126 (FIG. 4) in stainless steel Phytem ® 260 equivalent ferric stainless steel Kara from ArcelorMittal grade K44. |
| Magnetic shield: | Cylindrical torus in Fluxtrol ® |
| Power supply means | Rod 11 has been modified to incorporate the 3 $mm^2$ copper coaxial power supply. This coaxial cable changes the centre of gravity of the rod; it is thus balanced by compensating it with tungsten screws. |
| Thermocouples | Type K at the inlet and the outlet of the milling chamber. |
| Contactor | Cooper rotary contactor. |

The microbeads are made of zirconium oxide and have a diameter of 0.5 mm. The characteristics of the microbeads used for the tests are summarized in table 3 below:

TABLE 3

| Beads | 0.45/0.55 mm |
|---|---|
| Composition (% by mass) | 93% $ZrO_2$<br>5% $Y_2O_3$<br>2% others |
| Specific density | 6.0 g/cc |
| Bulk density | 3.7 kg/L |
| Vickers Hardness | 1250 HV1 |

The 0.5 mm microbeads are especially marketed as Zirmil® Y Ceramic Beads by Saint-Gobain.

The milling chamber of the mill has a capacity of 514 mL and is filled, by volume, in relation to its total volume and according to the tests, with 167 or 334 mL of the microbeads described above.

In operation, the microbeads are stirred by an agitator at a rotational speed which may vary, according to the examples, from 6 or 8 m/s. The agitator further comprises mixing discs made of chromium casting.

General Implementation Procedure According to the Invention ($3^{rd}$ Embodiment)

Preparation of the Starting Composition with Preheating:

A mixture of glycerol (425.0 g, 4.62 mol), catalyst and acetone (5.54 mol; 6.93 mol; 9.24 mol or 13.86 mol) are magnetically and vigorously stirred at 25° C., 40° C. or 56° C. in a 1 liter round-bottom three-neck flask equipped with a condenser (the experimental conditions are shown in table 4). In particular, the starting composition of example 10 of table 4 is preheated to 40° C. and that of example 14, to 25° C., while the compositions of the other examples are preheated to 56° C.

Introduction into the Three-Dimensional Mill:

The reaction medium is pumped using a peristaltic pump at a flow rate of 14 L/h or 42 L/h and the stream is introduced into the three-dimensional mill Dynomill ECM AP-05 described above, preheated or not according to the examples carried out. In particular, the heating device 20 is not operated in example 14, or allows heating to a temperature of 40° C. in example 10 and to a temperature of 56° C. in the other examples of table 4.

After a certain residence time in the mil, the reaction medium is analyzed as described below.

Sample Analysis

The analyses of the molecules resulting from the reaction were carried out by gas chromatography with a Hewlett Packard chromatograph (14009 Arcade, New York, United States). The chain consists of a manual injection system equipped with a septum (SPI), a Supelco 2-8047-U capillary column (15 m×0.25 mm i.e. and 0.25 μm film thickness, Alltech Part N° 31163-01), an oven, a flame ionization detector (FID, 70 eV, 300 μA, and 250° C.) and an acquisition system.

Sample Preparation

For each sample, the reaction medium (50 μL) and an n-decane-acetone solution (0.009M in acetone) are mixed.

Calibration

Calibration is performed by injecting several solutions containing the solketal at a varying concentration ($3.65\times10^{-4}$ M-$4.5625\times10^{-5}$ M) and the n-decane (0.009 M in acetone)-acetone solution at a fixed concentration.

The solketal (50 μL) and an n-decane-acetone solution (1:1, v/v) are mixed and represent a solketal concentration of $3.65\times10^{-4}$ M and an n-decane concentration of 0.009 M. A fraction of this mixture (50 μL) is diluted with a solution of n-decane-acetone (50 μL, 1:1, v/v) and represents a solketal concentration of $1.825\times10^{-4}$ M and an n-decane concentration of 0.009 M. A fraction of this mixture (50 μL) is diluted with a solution of n-decane-acetone (50 μL, 1:1, v/v) and represents a solketal concentration of $9.125\times10^{-5}$ M and an n-decane concentration of 0.009 M. A fraction of this mixture (50 μL) is diluted with a solution of n-decane-acetone (50 μL, 1:1, v/v) and represents a solketal concentration of $4.5625\times10^{-5}$ M and an n-decane concentration of 0.009 M.

Sample Analysis

The carrier gas used is hydrogen at a flow rate of 1 $mL\cdot min^{-1}$. Samples (2 μL) are manually injected with a septum-equipped programmable injector (SPI). The injector temperature is set to 250° C. with an oven temperature of 70° C. for 1 min and a temperature rise of 20° $C.\cdot min^{-1}$ to a temperature of 250° C. for 10 min.

The qualitative analysis of the compounds was performed by comparing the retention times with pure standards (acetone, n-decane, solketal, glycerol). The retention time of acetone is 0.417 min and the retention times of n-decane, solketal and glycerol are respectively 1.33 min, 2.36 min and 3.61 min. The qualitative analysis of the compounds was carried out on the basis of the calibration curve.

Reaction Conditions Used and Results

TABLE 4

| # | Catalyst | T (° C.) | Cat. conc. (mmol) | Total bulk vol. of beads (ml) | Acetone (mol) | Residence time (min) | Stirring speed (m/s)* | Flow rate (L/h) | Yield % |
|---|---|---|---|---|---|---|---|---|---|
| 1 | $FeCl_3$ | 56 | 1.57 | 334 | 13.86 | 3.4 | 8 | 14 | 99 |
| 2 | $FeCl_3$ | 56 | 1.57 | 334 | 13.86 | 1.8 | 8 | 14 | 99 |
| 3 | $FeCl_3$ | 56 | 1.57 | 334 | 9.24 | 2.37 | 8 | 14 | 99 |
| 4 | $FeCl_3$ | 56 | 1.57 | 334 | 6.93 | 1.3 | 8 | 14 | 84 |
| 5 | $FeCl_3$ | 56 | 0.785 | 334 | 9.24 | 2.37 | 8 | 14 | 84 |
| 6 | $AlCl_3$ | 56 | 1.57 | 334 | 9.24 | 2.37 | 8 | 14 | 99 |
| 7 | $MnSO_4$ | 56 | 1.57 | 334 | 9.24 | 2.37 | 8 | 14 | 99 |
| 8 | $CrCl_3$ | 56 | 1.57 | 334 | 9.24 | 2.37 | 8 | 14 | 99 |
| 9 | $FeCl_3$ | 56 | 1.57 | 334 | 5.54 | 1.3 | 8 | 14 | 46 |
| 10 | $FeCl_3$ | 40 | 1.57 | 334 | 9.24 | 2.37 | 8 | 14 | 67 |
| 11 | $FeCl_3$ | 56 | 1.57 | 167 | 9.24 | 3.19 | 8 | 14 | 60 |
| 12 | $FeCl_3$ | 56 | 1.57 | 334 | 9.24 | 2.37 | 6 | 14 | 75 |
| 13 | $FeCl_3$ | 56 | 1.57 | 334 | 9.24 | 1.85 | 8 | 42 | 68 |
| 14 | $FeCl_3$ | 25 | 1.57 | 334 | 9.24 | 44.48 | 8 | 14 | 11 |
| 15 | $H_2SO_4$ | 56 | 1.57 | 334 | 9.24 | 2.37 | 8 | 14 | 5 |
| 16 | $H_2SO_4$ | 56 | 187 (1 wt %) | 334 | 9.24 | 2.37 | 8 | 14 | 25 |
| 17 | HCl (1M) | 56 | 1.57 | 334 | 9.24 | 2.37 | 8 | 14 | 3 |
| 18 | $FeCl_2$ | 56 | 1.57 | 334 | 9.24 | 2.37 | 8 | 14 | 40 |
| 19 | $CuCl_2$ | 56 | 1.57 | 334 | 9.24 | 2.37 | 8 | 14 | <5 |
| 20 | CuCl | 56 | 1.57 | 334 | 9.24 | 2.37 | 8 | 14 | <5 |
| 21 | $CuSO_4$ | 56 | 1.57 | 334 | 9.24 | 2.37 | 8 | 14 | <5 |
| 22 | Betaine•HCl | 56 | 1.57 | 334 | 9.24 | 2.37 | 8 | 14 | 50 |
| 23 | HCl (37%) | 56 | 1.57 | 334 | 9.24 | 2.37 | 8 | 14 | 56 |
| 24 | p-Toluene sulfonic acid | 56 | 1.57 | 334 | 9.24 | 2.37 | 8 | 14 | 72 |
| 25 | Formic acid | 56 | 1.57 | 334 | 9.24 | 2.37 | 8 | 14 | 5 |

*the agitator stirring speed herein is the peripheral speed of the agitator (linear speed in m/s). For the mill type AP05, the agitator diameter being 6.5 cm, the peripheral speed of the agitator of 8 m/s corresponds to 2400 rpm. The peripheral speed is the rotational speed multiplied by the circumference of the agitator disc. As mentioned above, the optimized stirring speed will depend on the mill type used (laboratory mill as is the case here for the examples or industrial mill).

As can be seen, the method according to the invention allows very high yields to be obtained, depending in particular on the experimental conditions (non-arbitrary choice of catalyst, temperature advantageously of 56° C., microbeads volume, acetone concentration, etc.).

Example 13 shows for example that a residence time lower than 2 min (1.85 min) with a flow rate of 42 L/h does not allow for a solketal yield of 99% (but 68%), while example 2 shows that a residence time of 1.8 min with a flow rate of 14 L/h and a larger amount of acetone (13.86 mol versus 9.24 mol in example 11) allows for a yield of 99% to be obtained.

Generally, it was found by the inventors that the longer the residence time within the mill stationary chamber, the better the yield.

It also appears that the catalyst choice is important and that a Lewis hard acid catalyst comprising at least one transition metal like $FeCl_3$, $AlCl_3$, $CrCl_3$, $MnSO_4$ or a mixture thereof allows for very good yields to be obtained unlike the other catalysts tested.

Also, FIG. 3 and FIG. 4 corresponding to example 3 show that after a residence time of 1 min (FIG. 3), the method according to the invention allows the synthesis of solketal (retention time of 2.356 min) but glycerol (retention time of 3.607 min) also remains in the final composition; while with a residence time of 2.37 minutes (FIG. 4), there is no longer any peak corresponding to glycerol. Thus, the reaction is completed and has yielded solketal.

Of course, the parameters of the method (starting reagent concentration, throughput, etc.) can be optimized in order to obtain a continuous solketal synthesis, i.e. in a single pass. For example, the use of a lower throughput increases for example the residence time of the starting reagents/starting composition in the milling chamber and thus increases the solketal yield in a single pass.

The invention claimed is:

1. A method for preparing solketal ((2,2-dimethyl-1,3-dioxolan-4-yl)methanol) comprising the following steps:

(1) milling the following reactants, referred to as initial reactants, comprising at least: glycerol, a catalyst selected from a hard Lewis acid containing at least one transition metal, and acetone, the glycerol:acetone molar ratio being less than or equal to 0.8, at an ambient temperature greater than or equal to 50° C., in a three-dimensional mill with microbeads in liquid phase for a residence time of less than or equal to 15 minutes, and (2) collecting, at the outlet of the mill, a final composition comprising the solketal and, where applicable, one or more by-products corresponding to unreacted initial reactant(s) and/or 1,3-O-isopropylideneglycerol.

2. The method of preparation according to claim 1, further comprising the following step:

(3) separating the solketal from said by products.

3. The method of preparation according to claim 1, wherein the temperature during the milling step (1) is greater than or equal to 56° C.

4. The method of preparation according to claim 1, wherein the residence time during the milling step (1) is less than or equal to 10 minutes.

5. The method of preparation according to claim 4, wherein the residence time during the milling step (1) is less than or equal to 5 minutes.

6. The method of preparation according to claim 1, comprising a preliminary step (0) wherein the initial reactants, including at least glycerol and acetone are premixed to form an initial composition.

7. The method of preparation according to claim 6, wherein, during the preliminary step (0), the initial composition is preheated to a temperature greater than or equal to 56° C., so that the temperature during the milling step (1) is greater than or equal to 56° C.

8. The method of preparation according to claim 1, wherein, during the milling step (1), the initial reactants are heated inside the three-dimensional mill with microbeads, which includes a heating device.

9. The method of preparation according to claim 8, wherein the heating device is an induction heating device.

10. The method of preparation according to claim 1, wherein the pressure during the milling step (1) is within a range from 0.05 to 20 Mpa.

11. The method of preparation according to claim 10, wherein the pressure during the milling step (1) is within a range from 0.08 to 0.5 MPa.

12. The method of preparation according to claim 1, wherein the hard Lewis acid catalyst containing at least one transition metal is chosen from: $FeCl_3$, $AlCl_3$, $CrCl_3$, $MnSO_4$ or a mixture thereof.

13. The method of preparation according to claim 1, wherein the glycerol is anhydrous or has a water content by mass, relative to the total mass of the glycerol, within a range from 0 to 10%.

14. The method of preparation according to claim 13, wherein the glycerol is anhydrous or has a water content by mass, relative to the total mass of the glycerol, within a range from 0 to 5%.

15. The method of preparation according to claim 1, wherein the microbeads are spherical in shape and have an average diameter within a range from 0.05 mm to 4 mm.

16. The method of preparation according to claim 1, wherein the microbeads have a Vickers hardness, measured in accordance with standard EN ISO 6507-1, greater than or equal to 900 HV1.

17. The method of preparation according to claim 1, wherein the microbeads have real volumic mass within a range from 2 to 15 g/cm$^3$.

18. The method of preparation according to claim 1, wherein the three-dimensional mill with microbeads comprises at least:

a stationary mill chamber generally cylindrical in shape, extending along a longitudinal axis XX, said chamber being filled, at least in part, with said microbeads and comprising: at one end at least one inlet used to introduce said initial reactants and, at the other end, an outlet comprising a separation means capable of discharging only said final composition formed in said chamber; and an agitator arranged in the stationary mill chamber and taking the form of a rod extending along the longitudinal axis XX, said agitator being capable of setting in motion the totality of the microbeads/initial reactants.

19. The method of preparation according to claim 18, wherein the microbeads constitute by volume 50% to 85% of the total volume of the stationary chamber.

20. The method of preparation according to claim 19, wherein the microbeads constitute by volume 55% to 70% of the total volume of the stationary chamber.

21. The method of preparation according to claim 1, wherein the mill operates continuously.

* * * * *